United States Patent
Allen et al.

[11] Patent Number: 5,861,414
[45] Date of Patent: Jan. 19, 1999

[54] PIPERIDINEACETIC ACID DERIVATIVES USEFUL AS FIBRINOGEN ANTAGONIST AGENT

[75] Inventors: David George Allen; Colin David Eldred; William Leonard Mitchell, all of Herts, United Kingdom

[73] Assignee: Glaxo Group Limited, Greenford, England

[21] Appl. No.: 836,981

[22] PCT Filed: Dec. 21, 1995

[86] PCT No.: PCT/EP95/05043

§ 371 Date: May 29, 1997

§ 102(e) Date: May 29, 1997

[87] PCT Pub. No.: WO96/20192

PCT Pub. Date: Jul. 4, 1996

[30] Foreign Application Priority Data

Dec. 23, 1994 [GB] United Kingdom .................... 9426231
Feb. 17, 1995 [GB] United Kingdom .................... 9503133

[51] Int. Cl.⁶ ..................... A61K 31/445; G07D 401/04; C07D 401/14
[52] U.S. Cl. ........................... 514/316; 546/187; 546/199
[58] Field of Search ............................ 514/316; 546/187, 546/199

[56] References Cited

U.S. PATENT DOCUMENTS 3,681,382 8/1972 Gschwend .......................... 260/310 C
5,219,867 6/1993 Gollamudi ............................. 514/316

FOREIGN PATENT DOCUMENTS 0 542 363   5/1993   European Pat. Off. .
5255368   10/1993   Japan .
6234633   8/1994   Japan .

OTHER PUBLICATIONS

Cox D et al. Medicinal Research Reviews, 14(2), pp. 195–228, 1994.

*Primary Examiner*—Evelyn Huang
*Attorney, Agent, or Firm*—Bacon & Thomas, PLLC

[57] ABSTRACT

The invention provides the compounds of formula (I)

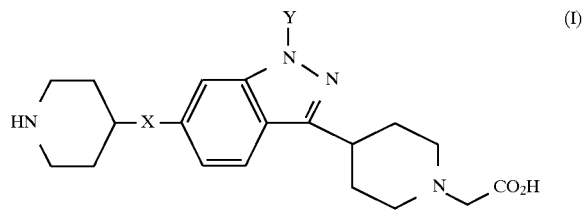

and pharmaceutically acceptable derivatives thereof, in which:

X represents either $CH_2$—$CH_2$ or $CH$=$CH$, and
Y represents a hydrogen atom or a phenylmethyl group, wherein the phenyl group is optionally substituted by one or more halogen atoms.

Compounds of formula (I) inhibit blood platelet aggregation.

11 Claims, No Drawings

PIPERIDINEACETIC ACID DERIVATIVES USEFUL AS FIBRINOGEN ANTAGONIST AGENT

This application is the national phase of PCT/EP95/05043, filed on Dec. 21, 1995, published as WO 96/20192 on Jul. 4, 1996.

This invention relates to acetic acid derivatives, to processes for their preparation, to pharmaceutical compositions containing such compounds and to their use in medicine.

It is widely accepted that the glycoprotein complex Gp IIb/IIIa is the fibrinogen binding site on platelets that mediates the adhesive function required for platelet aggregation and thrombus formation. We have now found a group of non-peptidic compounds which inhibit fibrinogen-dependent platelet aggregation by blocking the binding of fibrinogen to the putative fibrinogen receptor Gp IIb/IIIa complex.

The invention thus provides the compounds of formula (I)

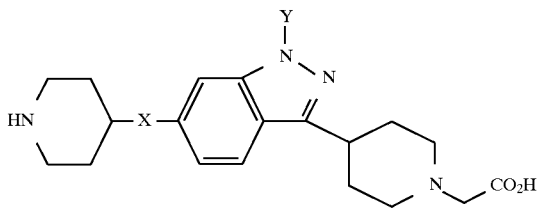

and pharmaceutically acceptable derivatives thereof, in which:

X represents either $CH_2-CH_2$ or $CH=CH$; and

Y represents a hydrogen atom or a phenylmethyl group, wherein the phenyl group is optionally substituted by one or more halogen atoms (where halogen represents fluorine, chlorine, bromine or iodine).

By pharmaceutically acceptable derivative is meant any pharmaceutically acceptable salt, solvate or ester, or salt or solvate of such ester, of the compounds of formula (I), or any other compound which upon administration to the recipient is capable of providing (directly or indirectly) a compound of formula (I) or an active metabolite or residue thereof.

It will be appreciated that, for pharmaceutical use, the salts referred to above will be the physiologically acceptable salts, but other salts may find use, for example in the preparation of compounds of formula (I) and the physiologically acceptable salts thereof.

Suitable physiologically acceptable salts of the compounds of formula (I) include acid addition salts formed with inorganic or organic acids (for example hydrochlorides, hydrobromides, sulphates, phosphates, benzoates, naphthoates, hydroxynaphthoates, p-toluenesulphonates, methanesulphonates, sulphamates, ascorbates, tartrates, salicylates, succinates, lactates, glutarates, glutaconates, acetates, tricarballylates, citrates, fumarates and maleates) and inorganic base salts such as alkali metal salts (for example sodium salts).

Other salts of the compounds of formula (I) include salts formed with trifluoroacetic acid.

It will be appreciated by those skilled in the art that the compounds of formula (I) may be modified to provide pharmaceutically acceptable derivatives thereof at any of the functional groups in the compounds. Of particular interest as such derivatives are compounds modified at the carboxyl function.

Thus compounds of interest include carboxylic acid esters of the compounds of formula (I). Examples of such esters include $C_{1-6}$alkyl esters.

It will be appreciated by those skilled in the art that the pharmaceutically acceptable derivatives of the compounds of formula (I) may be derivatised at more than one position It will be further appreciated by those skilled in the art that carboxylic acid ester derivatives of formula (I) may be useful as intermediates in the preparation of compounds of formula (I), or as pharmaceutically acceptable derivatives of formula (I), or both.

The term 'alkyl' as a group or part of a group means a straight or branched chain alkyl group, for example a methyl, ethyl, n-propyl, i-propyl, n-butyl, s-butyl or t-butyl group.

Preferably X represents $CH=CH$.

Preferably Y represents a hydrogen atom.

It is to be understood that the present invention encompasses all isomers of the compounds of formula (I) and their pharmaceutically acceptable derivatives, including all geometric, tautomeric and optical forms, and mixtures thereof (e.g. racemic mixtures).

Compounds in which X represents $CH=CH$ in the (E) configuration are particularly preferred.

Preferred compounds of the invention are:

{4-[1-(4-Fluoro-benzyl)-6-(2-piperidin-4-yl-(E)-vinyl)-1H-indazol-3-yl]-piperidin-1-yl}-acetic acid, and pharmaceutically acceptable derivatives thereof;

{4-[6-(2-Piperidin-4-yl-(E)-vinyl)-1H-indazol-3-yl]-piperidin-1-yl}acetic acid, and pharmaceutically acceptable derivatives thereof.

A particularly preferred compound of the invention is:

{4-[6-(2-Piperidin-4-yl-(E)-vinyl)-1H-indazol-3-yl]-piperidin-1-yl}acetic acid hydrochloride, and hydrates thereof.

Compounds of formula (I) inhibit blood platelet aggregation as demonstrated by studies performed on human washed and resuspended platelets (HRP) using a Born-type optical aggregometer (Born, G.V., 1962, Nature, 194, 927–929).

In view of their fibrinogen antagonist activity, the compounds of the present invention are of interest for use in human and veterinary medicine, particularly in the treatment of thrombotic disorders. Particular examples of thrombotic disorders are known in the art and include occlusive vascular diseases such as myocardial infarction, cardiac fatalities, angina, transient ischaemic attacks and thrombotic stroke, arteriosclerosis, vessel wall disease, peripheral vascular disease, nephropathy, retinopathy, postoperative thrombosis, pulmonary embolism, deep vein thrombosis and retinal vein thrombosis. The compounds of the invention are also of interest for use in the prophylactic treatment of peri- and postoperative complications following organ transplantation (particularly cardiac and renal), coronary artery bypass, peripheral artery bypass, angioplasty, thrombolysis and endarterectomy.

The compounds of the invention may also be useful for the treatment of other conditions in which the glycoprotein complex Gp IIb/IIIa or other integrin receptors are implicated. Thus, for example, the compounds of the invention may potentiate wound healing and be useful in the treatment of bone conditions caused or mediated by increased bone resorption. Particular examples of bone diseases are known in the art and include osteoporosis, hypercalcaemia of malignancy, osteopenia due to bone metastases, periodontal disease, hyperparathyroidism, periarticular erosions in rheumatoid arthritis, Paget's disease, immobilization-induced osteopenia and glucocorticoid treatment.

The compounds of the invention may also be useful for the treatment of certain cancerous diseases. For example, compounds of the invention may be of use to prevent or delay metastasis in cancer.

According to a further aspect of the invention, we provide a compound of formula (I) or a pharmaceutically acceptable derivative thereof for use in human or veterinary medicine, particularly for use in the treatment of thrombotic disorders.

According to another aspect of the invention, we provide a compound of formula (I) or a pharmaceutically acceptable derivative thereof for use in the treatment of a condition which is mediated through the Glycoprotein complex GpIIb/IIIa or other integrin receptor.

According to a further aspect of the invention, we provide a method of treating a human or animal subject suffering from a condition which is mediated through the Glycoprotein complex GpIIb/IIIa or other integrin receptor which comprises administering to said subject an effective amount of a compound of formula (I) or a pharmaceutically acceptable derivative.

According to another aspect of the invention, we provide the use of a compound of formula (I) or a pharmaceutically acceptable derivative thereof for the manufacture of a therapeutic agent for the treatment of thrombotic disorders.

According to a further aspect of the invention, we provide a method of treating a human or animal subject suffering from a thrombotic disorder, which method comprises administering to said subject an effective amount of a compound of formula (I) or a pharmaceutically acceptable derivative thereof.

It is to be understood that reference to treatment includes both treatment of established symptoms and prophylactic treatment, unless explicitly stated otherwise.

It will be appreciated that the compounds of the invention may advantageously be used in conjunction with one or more other therapeutic agents. Examples of suitable agents for adjunctive therapy include thrombolytic agents or any other compound stimulating thrombolysis or fibrinolysis and cytotoxic drugs. It is to be understood that the present invention covers the use of a compound of formula (I) or a pharmaceutically acceptable derivative thereof in combination with one or more other therapeutic agents.

The compounds of formula (I) and their pharmaceutically acceptable derivatives are conveniently administered in the form of pharmaceutical compositions. Thus, in another aspect of the invention, we provide a pharmaceutical composition comprising a compound of formula (I) or a pharmaceutically acceptable derivative thereof adapted for use in human or veterinary medicine. Such compositions may conveniently be presented for use in conventional manner in admixture with one or more physiologically acceptable carriers or excipients.

The compounds according to the invention may be formulated for administration in any suitable manner. The compounds may, for example, be formulated for topical administration or administration by inhalation or, more preferably, for oral or parenteral administration.

For oral administration, the pharmaceutical composition may take the form of, for example, tablets, capsules, powders, solutions, syrups or suspensions prepared by conventional means with acceptable excipients.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilising and/or dispersing agents. For administration by injection these may take the form of a unit dose presentation or as a multidose presentation preferably with an added preservative.

Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

As stated above, the compounds of the invention may also be used in combination with other therapeutic agents. The invention thus provides, in a further aspect, a combination comprising a compound of formula (I) or a pharmaceutically acceptable derivative thereof together with a further therapeutic agent, in particular a thrombolytic agent, or another inhibitor of platelet aggregation, such as aspirin.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A proposed daily dosage of a compound of formula (I) for the treatment of man is 0.01 mg/kg to 30 mg/kg, which may be conveniently administered in 1 to 4 doses. The precise dose employed will depend on the age and condition of the patient and on the route of administration. Thus, for example, a daily dose of 0.1 mg/kg to 10 mg/kg may be suitable for systemic administration.

Compounds of formula (I) and pharmaceutically acceptable derivatives thereof may be prepared by any method known in the art for the preparation of compounds of analogous structure.

Suitable methods for the preparation of compounds of formula (I) and pharmaceutically acceptable derivatives thereof are described below.

In the formulae that follow X and Y are as defined in formula (I) above unless otherwise stated; R represents a chlorine, bromine or iodine atom, or the group —OSO$_2$CF$_3$; Lg represents a leaving group, e.g. a methanesulphonate leaving group; and Ph represents a phenyl group optionally substituted by one or more halogen atoms.

Thus, according to a first process (A), compounds of formula (I) in which X represents CH=CH may be prepared by reacting a compound of formula (II)

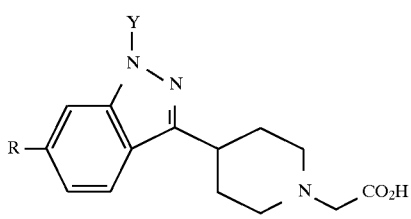

or a protected derivative thereof with the compound of formula (III)

or a protected derivative thereof. Conveniently the reaction is effected in the presence of a base, such as a tertiary amine; a transition metal catalyst, such as a palladium catalyst, for example a palladium triarylphosphine catalyst; a solvent; and at elevated temperature, for example at 80° to 120° C.

According to another process (B) compounds of formula (I) may be prepared by interconversion, utilising other compounds of formula (I) as precursors.

For example, compounds of formula (I) in which X represents $CH_2$—$CH_2$ may be prepared from the corresponding compounds of formula (I) in which X represents CH=CH by hydrogenation. The hydrogenation may be effected in the presence of a transition metal catalyst, such as Raney Nickel, or a palladium, platinum or rhodium catalyst. Conveniently the reaction is effected in a solvent, such as an alcohol (e.g. ethanol).

Alternatively, hydrogenation may be effected using diimide. Conveniently the diimide is generated in situ from a suitable salt, such as diazenedicarboxylic acid, dipotassium salt, and the reaction is effected in the presence of an acid, such as acetic acid, and a solvent, such as an alcohol (e.g. methanol).

Compounds of formula (I) in which Y is other than a hydrogen atom may be prepared from the corresponding compounds of formula (I) in which Y is a hydrogen atom by treatment with a reagent Lg—$CH_2$—Ph. Conveniently the reaction is effected in the presence of a base, such as an alkali metal hydride, in a solvent, such as a polar aprotic solvent, and at ambient temperature.

Suitable leaving atoms or groups in respect of Lg—$CH_2$—Ph are described in many standard texts on organic chemistry, for example in table 10.10 on page 357 of 'Advanced Organic Chemistry' by Jerry March, fourth edition (Wiley, 1992). It will be appreciated by a person skilled in the art that the choice of a particular leaving group in the above reaction may depend upon the compound of formula (I) desired, the group —$CH_2$—Ph and the reaction conditions employed.

As will be appreciated by those skilled in the art it may be necessary or desirable at any stage in the above described processes to protect one or more sensitive groups in the molecule to prevent undesirable side reactions.

Another process (C) for preparing compounds of formula (I) thus comprises deprotecting protected derivatives of compounds of formula (I). In a particular embodiment of this process compounds of formula (I) may be prepared from protected carboxyl derivatives of compounds of formula (I). In a further embodiment of this process, compounds of formula (I) may be prepared from protected amino derivatives of compounds of formula (I).

The protecting groups used in the preparation of compounds of formula (I) may be used in conventional manner.

See, for example, those described in 'Protective Groups in Organic Synthesis' by Theodora W. Green, second edition, (John Wiley and Sons, 1991), which also describes methods for the removal of such groups.

Particular carboxyl protecting groups include, for example, carboxylic acid ester groups such as carboxylic acid alkyl or aralkyl esters, for example where the alkyl or aralkyl portion of the ester function is methyl, ethyl, tert-butyl, methoxymethyl, benzyl, diphenylmethyl, triphenylmethyl or p-nitrobenzyl. When the ester is an unbranched alkyl (e.g. methyl) ester deprotection may be effected under conditions of either basic hydrolysis, for example using lithium hydroxide, or acidic hydrolysis, for example using hydrochloric acid. Tert-butyl and triphenylmethyl ester groups may be removed under conditions of acid hydrolysis, for example using formic or trifluoroacetic acid at ambient temperature or using hydrochloric acid in acetic acid. Benzyl, diphenylmethyl and nitrobenzyl ester groups may be removed by hydrogenolysis in the presence of a metal catalyst (e.g. palladium).

Particular amino protecting groups include, for example, aralkyl groups such as benzyl, diphenylmethyl or triphenylmethyl groups; and acyl groups such as N-benzyloxycarbonyl, t-butoxycarbonyl or trifluoroacetyl groups.

When a particular isomeric form of a compound of formula (I) is desired the required isomer may conveniently be separated using preparative high performance liquid chromatography (h.p.l.c.) applied to the final products of processes (A) to (C) above or applied prior to any final deprotection step in said processes.

Compounds of formula (II), or protected derivatives thereof, may be prepared using conventional chemistry. Compounds of formula (III), or protected derivatives thereof, are either known compounds or may be prepared using conventional chemistry, e.g. according to R. A. Perry et al, Can. J. Chem., 1976, 54(15), 2385–2401, incorporated herein by reference.

Certain intermediates described above are novel compounds, and it is to be understood that all novel intermediates herein form further aspects of the present invention. Compounds of formula (II) are key intermediates and represent a particular aspect of the present invention.

Conveniently, compounds of the invention are isolated following work-up as acid addition salts, e.g. trifluoroacetate salts. Pharmaceutically acceptable acid addition salts of the compounds of may be prepared from the corresponding trifluoroacetate salts by exchange of ion using conventional means, for example by neutralisation of the trifluoroacetate salt using a base such as aqueous sodium hydroxide, followed by addition of a suitable organic or inorganic acid. Inorganic base salts of the compounds of may also be prepared from the corresponding trifluoroacetate salts by addition of a suitable strong base such as sodium hydroxide.

Solvates (e.g. hydrates) of a compound of the invention may be formed during the work-up procedure of one of the aforementioned process steps.

The following Examples illustrate the invention but do not limit the invention in any way. All temperatures are in °C. Thin layer chromatography (T.l.c.) was carried out on silica plates. Preparative high performance liquid chromatography (h.p.l.c.) was carried out using a Dynamax 60 Å C18 8 μM 25 cm×41.4 mm i.d. column eluted with a mixture of solvents consisting of (i) 0.1% trifluoroacetic acid in water and (ii) acetonitrile, the eluant being expressed as the percentage of (ii) present in the solvent mixture, at a flow rate of 45 ml per minute. Analytical h.p.l.c. was carried out using a Dynamax 60 Å C18 8 μM 25 cm×4.6 mm i.d.

column eluted with a mixture of solvents consisting of (i) and (iii), 0.05% trifluoroacetic acid in acetonitrile, the eluant being expressed as the percentage of (iii) present in the solvent mixture, at a flow rate of 1 ml per minute. NMR was carried out on a Varian Unity 400 spectrometer, using $D_2O$ as solvent. Chemical shifts are given in δ ppm with respect to tetramethylsilane as internal chemical shift reference. The following abbreviations are used: Me=methyl, Et=ethyl, DMF=N,N-dimethylformamide, s=singlet, d=doublet, t=triplet and m=multiplet.

EXAMPLE 1

(i)1-[4-(2,4-Dibromo-benzoyl)-piperidin-1-yl]-ethanone 1,3-Dibromobenzene (65 ml, Aldrich) was added to a stirred mixture of 1-acetyl-piperidine-4-carbonyl chloride hydrochloride° (21.8 g, 115 mmol) and aluminium (III) chloride (34.5 g, 259 mmol) and the mixture heated at 95°–100° for 1.5 h. When cool, the mixture was poured into a mixture of ice-water (50 ml) and extracted with ethyl acetate (5×400 ml). The combined, dried ($Na_2SO_4$) organic extracts were evaporated in vacuo and the residue purified by flash chromatography over silica gel (Merck 9385). Gradient elution with ether—ethanol (gradient 99:1 to 90:10) afforded the title compound as an orange oil (16.7 g).
Ref°: EP-A-0 428 437

T.l.c. $SiO_2$ ($Et_2O$—EtOH, 9:1) Rf=0.23

(ii) (2,4-Dibromo-phenyl)-piperidin-4-yl-methanone hydrochloride

A stirred mixture of 1-[4-(2,4-dibromo-benzoyl)-piperidin-1-yl]-ethanone (11.00 g, 28.3 mmol) and aqueous 5M hydrochloric acid (60 ml) was heated under reflux under nitrogen for 7 h. The mixture was evaporated in vacuo to give the title compound as a white solid (10.8 g).

T.l.c. $SiO_2$ ($CH_2Cl_2$—EtOH-880$NH_3$, 89:10:1) Rf=0.17

(iii) (2.4-Dibromo-phenyl)-piperidin-4-yl-methylene-hydrazine

A stirred solution of (2,4-dibromo-phenyl)-piperidin-4-yl-methanone hydrochloride (7.04 g, 18.4 mmol), hydrazine (6.0 ml, 191 mmol), and ethanol (150 ml) was heated under reflux under nitrogen for 16 h. The cooled solution was evaporated in vacuo, treated with aqueous 1M sodium carbonate (50 ml), extracted with ether (5×100 ml), and the combined, dried ($Na_2SO_4$) organic extracts were evaporated in vacuo. The residue was purified by flash chromatography over silica gel (Merck 9385) eluting with dichloromethane-ethanol-880 ammonia (gradient 89:10:1 to 835:150:15) to give the title compound as a cream solid (5.71 g).

T.l.c. $SiO_2$ ($CH_2Cl_2$—EtOH-880 $NH_3$, 78:20:2) Rf=0.13 (minor) and Rf=0.16 (major)

(iv) 6-Bromo-3-piperidin-4-yl-1H-indazole hydrochloride

A stirred mixture of (2,4-dibromo-phenyl)-piperidin-4-yl-methylene-hydrazine (5.64 g, 15.6 mmol), sodium hydride (1.25 g of a 60% dispersion in oil, 31.2 mmol), and dry DMF (150 ml) was heated at 105° under nitrogen for 6.5 h. Further sodium hydride (200 mg of a 60% dispersion in oil, 5.00 mmol) was added and heating continued for 2 h. The mixture was evaporated in vacuo acidified to pH 1 by the addition of aqueous 2M hydrochloric acid, and then basified to pH 8 by the addition of aqueous 1M sodium carbonate. The mixture was extracted with ether (20×150 ml), and the combined, dried ($Na_2SO_4$) organic extracts were evaporated in vacuo. The residue was purified by flash chromatography over silica gel (Merck 9385), eluting with dichloromethane—ethanol—880 ammonia (gradient 89:10:1 to 78:20:2) to give the title compound as a cream-yellow solid (2.50 g).

T.l.c. $SiO_2$ ($CH_2Cl_2$—EtOH-880$NH_3$, 78:20:2) Rf=0.6

(v) [4-(6-Bromo-1H-indazol-3-yl)-piperidin-1-yl]-acetic acid tert-butyl ester

A mixture of 6-bromo-3-piperidin-4-yl-1H-indazole hydrochloride (500 mg, 1.78 mmol), tert-butyl bromoacetate (0.29 ml, 1.78 mmol), sodium bicarbonate (150 mg, 1.87 mmol), and DMF (10 ml) was stirred at +23° under nitrogen for 18 h The mixture was evaporated in vacuo, treated with aqueous saturated sodium bicarbonate (25 ml), and extracted with ethyl acetate (50 ml). The dried ($Na_2SO_4$) organic layer was evaporated in vacuo onto silica gel (Merck 7734). Purification by flash chromatography over silica gel (Merck 9385), eluting with dichloromethane—ethanol—880 ammonia (gradient 967:30:3 to 945:50:5) afforded the title compound as fine white crystals (347 mg).

T.l.c. $SiO_2$ ($CH_2Cl_2$—EtOH-880 $NH_3$, 945:50:5) Rf=0.27

(vi) {4-[6-Bromo-1-(4-fluoro-benzyl)-1H-indazol-3-yl]-piperidin-1-yl}-acetic acid tert-butyl ester Sodium hydride (42 mg of a 60% dispersion in oil, 1.05 mmol) was added to a stirred solution of [4-(6-bromo-1H-indazol-3-yl)-piperidin-1-yl]-acetic acid tert-butyl ester (332 mg, 0.84 mmol) in DMF (7 ml) and after 30 min, a solution of 4-fluorobenzyl bromide (0.105 ml, 0.84 mmol), in DMF (7 ml) was added. The mixture stirred at +23° under nitrogen for 16 h, treated with water (25 ml), extracted with ethyl acetate (3×50 ml) and the combined, dried ($Na_2SO_4$) organic extracts were evaporated in vacuo to give an oil. This oil was purified by flash chromatography over silica gel (Merck 9385) eluting with dichloromethane—ethanol—880 ammonia (967:30:3) to give impure title compound. This was further purified by flash chromatography over silica gel (Merck 9385) eluting with ethyl acetate—cyclohexane (1:2) to give the title compound as a colourless oil (290 mg).

T.l.c. $SiO_2$ ($CH_2Cl_2$—EtOH-880$NH_3$, 967:30:3) Rf=0.37

(vii) 4-(2-Hydroxy-ethyl)-piperidine-1carboxylic acid tert-butyl ester

A mixture of 4-(2-hydroxy-ethyl)piperidine (53.2 g, 0.412 mol; Acros Chimica NV), 1,4-dioxan (250 ml) and 2N aqueous sodium hydroxide (200 ml) was treated portionwise, over 15 min, with di-ert-butyl dicarbonate (95.4 g, 0.437 mol) at 25°. The mixture was stirred at 25° for 20 h and evaporated in vacuo. The aqueous residue was diluted with water (1000 ml) and extracted with diethyl ether (3×600 ml). The combined, dried ($MgSO_4$) organic extracts were evaporated in vacuo to give the title compound as a pale-yellow oil (94.5 g 0.412 mol, 100%).

T.l.c. $SiO_2$ cyclohexane: diethyl ether (5:1) Rf=0.1

(viii) 4-(2-Bromo-ethyl)-piperidine-1-carboxylic acid tert-butyl ester

A mixture of 4-(2-hydroxy-ethyl)-piperidine-1-carboxylic acid tert-butyl ester (94.0 Og 0.41 mol), carbon tetrabromide (198.7 g 0.6 mol) and dichloromethane (1500 ml) at 0° under nitrogen was treated portionwise, over 45 min, with triphenylphosphine (135.2 g 0.515 mol). The mixture was stirred for 1 h at 10° and 1 h at 25° and then evaporated in vacuo. The residue was purified by flash column chromatography on silica gel (Merck 9385), eluant cyclohexane: ethyl acetate (15:1, gradient to 10:1) to give the title compound as a clear liquid (81.8 g, 0.28 mol, 68%).

T.l.c. SiO$_2$ cyclohexane: diethyl ether (5:1) Rf=0.4

(ix) 4-Vinyl-piperidine-1-carboxylic acid tert-butyl ester

A solution of 4(2-bromo-ethyl)-piperidine-1-carboxylic acid tert-butyl ester (81.5 g 0.279 mol) in dry tetrahydrofuran (1000 ml) under nitrogen at 20° was treated portionwise, over 30 min, with potassium tert-butoxide (63.2 g 0.563 mol). The mixture was stirred at 25° for 3 h and partitioned between saturated aqueous ammonium chloride (1000 ml) and diethyl ether (500 ml). The aqueous phase was extracted with diethyl ether (4×500 ml) and the combined, dried (MgSO$_4$) extracts were evaporated in vacuo. The residue was purified by flash column chromatography on silica gel (Merck 9385) eluant cyclohexane: diethyl ether (19:1) to give the title compound as an orange oil (37.1 g, 0.176 mol, 63%).

Mass spectrum m/z=212 [MH$^+$]

T.l.c. SiO$_2$ cyclohexane: diethyl ether (10:1) Rf=0.3

(x) 4-{2-[3-(1-tert-Butoxycarbonylmethyl-piperidin-4-yl)-1-(4-fluoro-benzyl)-1H-indazol-6-yl]-(E)-vinyl}-piperidine-1-carboxylic acid tert-butyl ester A stirred mixture of {4-[6-bromo-1-(4-fluoro-benzyl)-1H-indazol-3-yl]-piperidin-1-yl}-acetic acid tert-butyl ester (286 mg, 0.57 mmol), 4-vinyl-piperidine-1-carboxylic acid tert-butyl ester (120 mg, 0.57 mmol), lithium chloride (24 mg, 0.57 mmol), triethylamine (0.24 ml, 1.71 mmol), palladium (II) acetate (8 mg 0.03 mmol), tri-o-tolylphosphine (35 mg, 0.11 mmol), and DMF (5 ml) was heated at 105° (oil-bath temperature) under nitrogen for 18 h. When cool, the mixture was evaporated in vacuo, treated with aqueous saturated sodium bicarbonate (20 ml), and extracted with ethyl acetate (2×20 ml). The combined, dried (Na$_2$SO$_4$) organic extracts were evaporated, and the residue purified by flash chromatography over silica gel (Merck 9385). Elution with ethyl acetate —cyclohexane (1:2) afforded impure fractions and pure fractions (I). The impure fractions were purified by flash chromatography over silica gel (Merck-9385) eluting with ethyl acetate—cyclohexane (gradient 1:4 to 1:2) to give pure fractions (II). The pure fractions (I) and (II) were combined to give the title compound as a pale yellow oil (195 mg).

T.l.c. SiO$_2$ (EtOAc-Cyclohexane, 1:2) Rf=0.26

(xi) {4-[1-(4-Fluoro-benzyl)-6-(2-piperidin-4-yl-(E)-vinyl)-1H-indazol-3-yl]-piperidin-1-yl}-acetic acid trifluoroacetate 4-{2-[3-(1-tert-Butoxycarbonylmethyl-piperidin-4-yl)-1-(4-fluoro-benzyl)-1H-indazol-6-yl]-(E)-vinyl}piperidine-1-carboxylic acid tert-butyl ester (181 mg, 0.29 mmol) was stirred in trifluoroacetic acid (10 ml), containing water (1 ml) at +25° for 2.5 h. The solution was evaporated in vacuo and the residue purified by preparative h.p.l.c. using standard conditions (gradient profile 10–30% (ii) in 1 min, 30% (ii) isochratic for 30 min, 30–10% (ii) in 1 min), but with a flow rate of 20 ml/min. The collected eluant (Rf 21.2 min) was evaporated in vacuo and triturated with ether to give the title compound as a cream solid (80 mg). Analytical h.p.l.c. (gradient profile 10–90% (ii) in 25 min) Rf 12.5 min Analysis found: C, 50.2; H, 4.8; N, 7.4;

C$_{28}$H$_{33}$FN$_4$O$_2$. 2.85 CF$_3$CO$_2$H requires: C, 50.5; H, 4.5; N, 7.0%

EXAMPLE 2

(i) 4-{2-[3-(1-tert-Butoxycarbonylmethyl-piperidin-4-yl)-1H-indazol-6-yl]-(E)-vinyl}-piperidine-1-carboxylic acid tert-butyl ester A mixture of [4-(6-bromo-1H-indazol-3-yl)-piperidin-1-yl]-acetic acid tert butyl ester (1.34 g, 3.40 mmol), 4-vinyl-piperidine-1-carboxylic acid tert-butyl ester (0.75 g, 3.57 mmol), triethylamine (1.4 ml, 10.2 mmol), palladium (ii) acetate (0.050 g, 0.22 mmol) and tri(o-tolyl)phosphine (0.210 g, 0.6 mmol) in DMF (60 ml) was stirred at 120° under nitrogen for 16 h. The mixture was evaporated in vacuo and purified by flash chromatography on silica gel (Merck 9385), eluant ethyl acetate:cyclohexane:triethylamine (50:50:2→100:0:2), to give the title compound as a yellow solid (1.18 g, 66%).

T.l.c. SiO$_2$ (CH$_2$Cl$_2$:EtOH:880 NH$_3$ 95:5:0.5) Rf=0.32

(ii) {4-[6-(2-Piperidin-4-yl-(E)-vinyl)-1H-indazol-3-yl]-piperidin-1-yl}-acetic acid trifluoroacetate A solution of 4-{2-[3-(1-tert-butoxycarbonylmethyl-piperidin-4-yl)-1H-indazol-6-yl]-(E)-vinyl}-piperidine-1-carboxylic acid tert-butyl ester (0.202 g, 0.385 mmol) in trifluoroacetic acid (5 ml) was stirred at 23° for 3 h. The solvent was evaporated in vacuo and the residue was triturated with ether to give the title compound as an off-white solid (0.228 g, 97%)

Mass spectrum m/z 369.4 [MH$^+$]

Analysis found: C, 49.5; H, 5.0; N, 9.0;

C$_2$H$_{28}$N$_4$O$_2$ 2.15 C$_2$HF$_3$O$_2$ requires: C, 49.5; H, 5.0; N, 9.1%

(iii) {4-[6-(2-Piperidin-4-yl-(E)-vinyl)-1H-indazol-3-yl]-piperidin-1-yl}acetic acid 4-{2-[3-(1-tert-Butoxycarbonylmethyl-piperidin-4-yl)-1H-indazol-6-yl]-(E)-vinyl}-piperidine-1-carboxylic acid tert-butyl ester (54.0 g) was added portionwise (ca. 9 portions) over 0.75 h to a stirred solution of 5M hydrochloric acid (270 ml) at 20°–25°, and the mixture was stirred at 20°–23° for 18 h. 880 Ammonia (54 ml) was added dropwise with caution over 0.75 h, maintaining the temperature between 18°–26°. The resulting solution (pH 1–2) was filtered through 1 micron graded glass fibre filter paper and the filter washed through with water (54 ml). Further 880 ammonia (36.2 ml) was added dropwise over 0.5 h maintaining the temperature between 22°–26° (pH 9–9.5). The suspension was stirred at 22°–230° for 3 h, and the resulting precipitate filtered off, washed with water (2×148 ml) and dried in vacuo to give the title compound as a white solid (27.6 g).

Analysis Found: C, 66.7; H, 8.0; N, 14.95.

C$_{21}$H$_{28}$N$_4$O$_2$ requires: C, 68.5; H, 7.7; N, 15.2.

(iv) {4-[6-(2-Piperidin-4-yl-(E)-vinyl)-1H-indazol-3-yl]-piperidin-1-yl}-acetic acid, hydrochloride hydrate A suspension of {4-[6-(2-piperidin-4-yl-(E)-vinyl)-1H-indazol-3-yl]-piperidin-1-yl}-acetic acid (20.5 g) in water (41 ml) was carefully adjusted to pH 5.7 with 2M hydrochloric acid (27 ml). The resulting solution was filtered through 1 micron graded glass fibre filter paper and the filter washed through with water (2×20.5 ml). Isopropanol (219 ml) was added dropwise to the stirred filtrate over 0.25 h at 22°, and the solution was seeded with product crystals (10 mg). The mixture was allowed to crystallise for 0.5 h, stirred at 22° for 1.5 h, and further isopropanol (219 ml) was added slowly over 0.5 h. After stirring for a further 3 h at 22° the suspension was filtered. The filter cake was washed with a mixture of isopropanol:water (4:1, 2×41 ml) and dried in vacuo at 45° for 6 h to give the title compound as a white solid (14.1 g).

Analysis Found: C, 57.7; H, 7.4; N, 12.9; Cl, 8.2;

C$_{21}$H$_{28}$N$_4$O$_2$.HCl.1.63H$_2$O requires: C, 58.1; H, 7.5; N, 12.9; Cl, 8.2.

Water Assay Found: 6.75% w/w H$_2$O;

1.63 H$_2$O Requires 6.76% w/w H$_2$O.

NMR: 1.74,m(2H); 2.11,m(2H); 2.23,m(4H); 2.59,m(1H); 3.14,d of t(2H), J=3.1 Hz, 12.9 Hz; 3.21,broad m(2H); 3.32, broad m(1H); 3.55,d of t(2H), J=12.9 Hz, 3.1 Hz; 3.74,broad m(2H); 3.78,s(2H); 6.44,d of d(1H), J=16.1 Hz, 6.6 Hz; 6.66, d(1H), J=16.1 Hz; 7.37,d of d(1H), J=8.6 Hz, 1.1 Hz; 7.52,s(1H); 7.76,d(1H), J=8.6 Hz.

EXAMPLE 3

(i) 4-{2-[3-(1-tert-Butoxycarbonylmethyl-piperidin-4-yl)-1-(3,4-dichloro-benzyl)-1H-indazol-6-yl]-(E)-vinyl}-piperidine-1-carboxylic acid tert-butyl ester Sodium hydride (12.2 mg; 0.304 mmol) was added to a stirred solution of 4-{2-[3-(1-tert-butoxycarbonylmethyl-piperidin-4-yl)-1H-indazol-6-yl]-(E)-vinyl} piperidine-1-carboxylic acid tert-butyl ester (145 mg; 0.276 mmol) in dry DMF (5 ml) and the mixture was stirred at 23° under nitrogen for 25 min. 3,4-Dichlorobenzyl chloride (0.043 ml, 0.304 mmol; Aldrich) was added, and the mixture was stirred at 23° for 18 h. The solvent was evaporated in vacuo and the residue partitioned between water (25 ml) and ethyl acetate (3×20 ml). The organic layers were washed with 50:50 brine: water (30 ml) and brine, dried ($MgSO_4$) and evaporated in vacuo to give a yellow oil (193 mg). Purification by flash chromatography on silica gel (Merck 9385), eluting with ether: cyclohexane 70:30 gave the title compound as a colourless oil (117 mg; 62%).

T.l.c. $SiO_2$ ($CH_2Cl_2$:EtOH:880$NH_3$ 95:5:0.5) Rf=0.7

(ii) {4-[1-(3,4-Dichloro-benzyl)-6-(2-piperidin-4-yl-(E)-vinyl)-1H-indazol-3-yl]-piperidin-1-yl}-acetic acid trifluoroacetate 4-{2-[3-(1-Tert-butoxycarbonylmethyl-piperidin-4-yl)-1-(3,4-dichloro-benzyl)-1H-indazol-6-yl]-(E)-vinyl}-piperidine-1-carboxylic acid tert-butyl ester (110 mg; 0.161 mmol) was stirred at 23° in trifluoroacetic acid (4 ml) under nitrogen for 5 h. The solvent was evaporated in vacuo and the residue triturated with dry ether to give the title compound as a white solid (90 mg; 74%).
Mass spectrum m/z 527 (MH$^+$)
Assay found: C, 51.2; H, 4.7; N, 7.6;
$C_{28}H_{32}Cl_2N_4O_2$.2$CF_3CO_2H$ requires C, 50.9; H, 4.5; N, 7.4.

EXAMPLE 4

(i) 4-{2-[3-(1-tert-Butoxycarbonylmethyl-piperidin-4-yl)-1-(4-chloro-benzyl)-1H-indazol-6-yl]-(E)-vinyl}-piperidine-1-carboxylic acid tert-butyl ester A solution of 4-{2-[3-(1-tert-butoxycarbonylmethyl-piperidin-4-yl)-1H-indazol-6-yl]-(E)-vinyl}-piperidine-1-carboxylic acid tert-butyl ester (0.29 g, 0.553 mmol) in dry DMF (5 ml) was stirred under nitrogen and treated with sodium hydride (0.024 g, 0.608 mmol, 60% dispersion in oil). The mixture was stirred for 0.5 h and a solution of 4-chlorobenzyl chloride (0.090 g, 0.559 mmol; Aldrich) in DMF (5 ml) was added). The mixture was stirred at 23° for 16 h, evaporated in vacuo, treated with water (10 ml) and extracted with dichloromethane (3×20 ml). The extracts were evaporated in vacuo and purified by flash chromatography on silica gel (Merck 9385), eluant ether:cyclohexane:triethylamine (50:50:2 to 100:0:2), to give the title compound as a colourless gum (0.157 g, 44%).

T.l.c. $SiO_2$ ($CH_2Cl_2$:EtOH:880$NH_3$ 95:5:0.5) Rf=0.40.

(ii) (4-{1-(4-Chloro-benzyl)-6-[2-piperidin-4-yl-(E)-vinyl]-1H-indazol-3-yl}-piperidin-1-yl)-acetic acid trifluoroacetate A solution of 4-{2-[3-(1-tert-butoxycarbonylmethyl-piperidin-4-yl)-1-(4-chloro-benzyl)-1H-indazol-6-yl]-(E)-vinyl}-piperidine-1-carboxylic acid tert-butyl ester (0.152 g, 0.234 mmol) in trifluoroacetic acid (4 ml) was stirred at 23° for 3 h. The solvent was removed in vacuo and the residue was triturated with ether to give the title compound as an ivory solid (0.148 g, 86%).
Mass spectrum m/z 493 [MH$^+$]
Analysis found: C, 52.6; H, 5.0; N, 7.5;
$C_{28}H_{33}ClN_4O_2$. 2.15 $C_2HF_3O_2$ requires: C, 52.6; H, 4.8; N, 7.6%.

EXAMPLE 5

(i) 4-{2-[3-(1-tert-Butoxycarbonylmethyl-piperidin-4-yl)-1H-indazol-6-yl]-ethyl}-piperidine-1-carboxylic acid tert-butyl ester A solution of 4-{2-[3-(1-tert-butoxycarbonylmethyl-piperidin-4-yl)-1H-indazol-6-yl]-(E)-vinyl}-piperidine-1-carboxylic acid tert-butyl ester (0.84 g, 1.60 mmol) in ethanol (80 ml) was hydrogenated over palladium on carbon (10%, 0.14 g) for 4 h. The catalyst was filtered off and the filtrate was evaporated in vacuo to give the title compound as an ivory solid (0.80 g, 95%).
Mass spectrum m/z 527 [MH$^+$].

(ii) 4-{2-[3-(1-tert-Butoxycarbonylmethyl-piperidin-4-yl)-1-(4-chloro-benzyl)-1H-indazol-6-yl]-ethyl}-piperidine-1carboxylic acid tert-butyl ester A solution of 4-{2-[3-(l-tert-butoxycarbonylmethyl-piperidin-4-yl)-1H-indazol-6-yl]-ethyl}-piperidine-1carboxylic acid tert-butyl ester (0.25 g, 0.475 mmol) in dry DMF (5 ml) was treated with sodium hydride (0.021 g, 0.523 mmol, 60% dispersion in oil) and the mixture was stirred at 23° under nitrogen for 30 min. A solution of 4-chlorobenzyl chloride (0.080 g, 0.497 mmol; Aldrich) in DMF (5 ml) was added and the mixture was stirred at 23° for 20 h. The solvent was removed in vacuo, the residue treated with water and extracted with dichloromethane (3×30 ml); the extracts were evaporated in vacuo to give an orange gum. Purification by flash chromatography on silica gel (Merck 9385), eluant ether: cyclohexane:triethylamine (50:50:2 to 100:0:2), gave the title compound as a colourless gum (0.107 g, 35%).

T.l.c. $SiO_2$ (ether:triethylamine 1:0.02) Rf=0.52.

(iii) {4-[1-(4-Chloro-benzyl)-6-(2piperidin-4-yl-ethyl)-1H-indazol-3-yl-piperidin-1-yl]-acetic acid trifluoroacetate A solution of 4-{2-[3-(1-tert-butoxycarbonylmethyl-piperidin-4-yl)-1-(4-chloro-benzyl)-1H-indazol-6-yl]-ethyl}-piperidine-1-carboxylic acid tert-butyl ester (0.107 g, 0.164 mmol) in trifluoroacetic acid (4 ml) was stirred at 23° for 2 h, evaporated in vacuo and the residue was triturated with ether to give the title compound as white solid (0.113 g, 92%).
Mass spectrum m/z 495.5 [MH$^+$]
Analysis found: C, 52.3; H, 5.2; N, 7.8;
$C_{28}H_{35}ClN_4O_2$. 2.2$C_2HF_3O_2$ requires: C, 52.2; H, 5.0; N, 7.5%.

EXAMPLE 6

(i) 4-{2-[3-(1-tert-Butoxycarbonylmethyl-piperidin-4-yl)-1-(4-fluoro-benzyl)-1H-indazol-6-yl]-(E)-vinyl)-piperidine-1-carboxylic acid tert-butyl ester Sodium hydride (176 mg of a 60% dispersion in oil, 4.40 mmol) was added to a solution of 4-{2-[3-(1-tert-butoxycarbonylmethyl-piperidin-4-yl)-1H-indazol-6-yl]-(E)-vinyl}-piperidine-1-carboxylic acid tert-butyl ester (1.90 g, 3.62 mmol) in dry DMF (80 ml) under nitrogen and stirred at +23° for 30 min. 4-Fluorobenzyl bromide (0.52 ml, 4.19 mmol; Aldrich) was added and stirring continued for 18 h. The mixture was evaporated in vacuo, treated with water (1 00 ml), and extracted with ethyl acetate (3×100 ml). The combined, dried ($Na_2SO_4$) organic extracts were evaporated onto silica gel (Merck 7734, 20 ml) and this purified by flash chromatography over silica gel (Merck 9385). Elution with ether—cyclohexane —triethylamine (gradient 25:73:2 to 50:48:2), gave the title compound as a pale yellow oil (920 mg).

T.l.c. $SiO_2$ (EtOAc-cyclohexane, 1:2) Rf=0.26

(ii) {4-[1-(4-Fluoro-benzyl)-6-(2-piperidin-4-yl-(E)-vinyl)-1H-indazol-3-yl]-piperidin-1-yl}-acetic acid hydrochloride A mixture of 4-{2-[3-(1-tert-butoxycarbonylmethyl-piperidin-4-yl)-1-(4-fluoro-benzyl)-1H-indazol-6-yl]-(E)-vinyl}-piperidine-1-carboxylic acid tert-butyl ester (400 mg, 0.63 mmol) in aqueous 5M hydrochloric acid (80 ml) was stirred at +23° under nitrogen for 4 h. The solution was evaporated in vacuo and the residue triturated with ether to give the title compound as a cream solid (299 mg).
Mass spectrum m/z 477 ($MH^+$)

EXAMPLE 7

(i) 4-{2-[1-Benzyl-3-(1-tert-butoxycarbonylmethyl-piperidin-4-yl)-1H-indazol-6-yl]-(E)-vinyl}-piperidine-1-carboxylic acid tert-butyl ester A solution of 4{-2-[3-(1-tert-butoxycarbonylmethyl-piperidin-4-yl)-1H-indazol-6-yl]-(E)-vinyl}-piperidine-1-carboxylic acid tert-butyl ester (152 mg, 0.29 mmol) in dry DMF (2 ml) under nitrogen was treated with sodium hydride (5 mg of a 60% dispersion in oil, 0.37 mmol) and stirred at +23° for 20 min. The solution was treated with a solution of benzyl bromide in dry DMF (0.1 ml of 3.14M solution, 0.314 mmol; Aldrich). The resulting mixture was stirred at +23° for 24 h and concentrated in vacuo. The residue was dissolved in dichloromethane (100 ml) and the solution washed with water (2×25 ml). The dried ($MgSO_4$) organic layer was concentrated in vacuo onto silica (Merck 9385); purification by flash chromatography eluting with ether—cyclohexane (1:1) gave the title compound as a white foam (102 mg).

T.l.c. $SiO_2$ ($Et_2O$) Rf=0.45

(ii) {4-[1-Benzyl-6-(2-piperidin-4-yl-(E)-vinyl)-1H-indazol-3-yl]-piperidin-1-yl}-acetic acid trifluoroacetate 4-{2-[1-Benzyl-3-(1-tert-butoxycarbonylmethyl-piperidin-4-yl]-1H-indazol-6-yl]-(E)-vinyl}-piperidine-1carboxylic acid tert-butyl ester (95 mg, 0.154 mmol) was treated with trifluoroacetic acid (2 ml) and the mixture stirred under nitrogen for 18 h. The solution was concentrated in vacuo and the residue dried in vacuo for 1 h. The resulting yellow gum was saturated with dry diethyl ether (5 ml); the supernatant was decanted off and the solid was washed with ether (5 ml) and dried in vacuo at 60° for 18 h to give the title compound (94 mg) as a pale yellow solid (94 mg).
Mass spectrum m/z 459.4 ($MH^+$)
Analysis found: C, 55.2; H, 5.1; N, 8.0;
$C_{28}H_{34}N_4O_2$. 2.1 $C_2HF_3O$ requires C, 55.4; H, 5.2; N, 8.0%

EXAMPLE 8

Inhibition of platelet aggregation by compounds of the invention was determined according to the following procedure. Citrated whole blood (1 part 3.8% w/v trisodium citrate; 9 parts blood) was obtained from human volunteers, free of medication for at least 10 days prior to donation. The blood was treated with aspirin (0.1 mM) and prostacyclin (0.06 μM) prior to centrifugation (1400 g, 4 minutes, 20° C.). The supernatant platelet-rich plasma (PRP) was isolated and further centrifuged (1400 g, 10 minutes, 20° C.) to sediment the platelets. The supernatant was discarded and the platelet pellet resuspended into a physiological salt solution (HEPES 5 mM, $NaHCO_3$ 12 mM, NaCl 140 mM, $KH_2PO_4$ 0.74 mM, D-Glucose 5.6 mM and KCl 2.82 mM) adjusted to pH 6.4. This platelet suspension was centrifuged (1400 g, 8 minutes, 20° C.) and the resultant platelet pellet was resuspended into the physiological salt solution adjusted to pH 7.4. The resultant washed-platelet preparation was diluted to give a final platelet count of $3 \times 10^8/l$. Purified human fibrinogen (Knight, L.C. et al., 1981 Thromb. Haemostasis, 46, (3), 593–596), $Ca^{2+}$ and $Mg^{2+}$ were added back to the washed platelet preparation to give final concentrations of 0.5 mg/ml, 1 mmol and 0.5 mmol respectively. Platelet aggregation was quantified using a turbidometric method. Test compounds were incubated with the washed platelets (37° C.) for 5 minutes prior to the addition of 1 μM of the platelet aggregatory agonist U-46619 (a stable thromboxane $A_2$-mimetic). The inhibitory potency of the test compounds was expressed as an $IC_{50}$ value, which is defined as the concentration of the compound required to inhibit platelet aggregation by 50%.

The following $IC_{50}$ values were obtained for compounds of the invention:

| Example No. | $IC_{50}$(nM) |
|---|---|
| 1 (xiii) | 126 |
| 2 (ii) | 92 |
| 2 (iv) | 67 |
| 3 (ii) | 74 |
| 4 (ii) | 72 |
| 5 (iii) | 80 |
| 6 (ii) | 110 |
| 7 (ii) | 107 |

EXAMPLE 9

Tablets

| a) | | |
|---|---|---|
| | Compound of the invention | 5.0 mg |
| | Lactose | 95.0 mg |
| | Microcrystalline Cellulose | 90.0 mg |
| | Cross-linked polyvinylpyrrolidone | 8.0 mg |
| | Magnesium Stearate | 2.0 mg |
| | Compression weight | 200.0 mg |

The compound of the invention, microcrystalline cellulose, lactose and cross-linked polyvinylpyrrolidone are sieved through a 500 micron sieve and blended in a suitable mixer. The magnesium stearate is sieved through a 250 micron sieve and blended with the active blend. The blend is compressed into tablets using suitable punches.

| b) | | |
|---|---|---|
| | Compound of the invention | 5.0 mg |
| | Lactose | 165.0 mg |
| | Pregelatinised Starch | 20.0 mg |
| | Cross-linked polyvinylpyrrolidone | 8.0 mg |
| | Magnesium Stearate | 2.0 mg |
| | Compression weight | 200.0 mg |

The compound of the invention, lactose and pregelatinised starch are blended together and granulated with water. The wet mass is dried and milled. The magnesium stearate and cross-linked polyvinylpyrrolidone are screened through a 250 micron sieve and blended with the granule. The resultant blend is compressed using suitable tablet punches.

EXAMPLE 10

Capsules

| a) | Compound of the invention | 5.0 mg |
|---|---|---|
| | Pregelatinised Starch | 193.0 mg |
| | Magnesium Stearate | 2.0 mg |
| | Fill weight | 200.0 mg |

The compound of the invention and pregelatinised starch are screened through a 500 micron mesh sieve, blended together and lubricated with magnesium stearate, (meshed through a 250 micron sieve). The blend is filled into hard gelatine capsules of a suitable size.

| b) | Compound of the invention | 5.0 mg |
|---|---|---|
| | Lactose | 177.0 mg |
| | Polyvinylpyrrolidone | 8.0 mg |
| | Cross-linked polyvinylpyrrolidone | 8.0 mg |
| | Magnesium Stearate | 2.0 mg |
| | Fill weight | 200.0 mg |

The compound of the invention and lactose are blended together and granulated with a solution of polyvinylpyrrolidone. The wet mass is dried and milled. The magnesium stearate and cross-linked polyvinylpyrrolidone are screened through a 250 micron sieve and blended with the granules. The resultant blend is filled into hard gelatine capsules of a suitable size.

EXAMPLE 11

Syrup

| a) | Compound of the invention | 5.0 mg |
|---|---|---|
| | Hydroxypropyl Methylcellulose | 45.0 mg |
| | Propyl Hydroxybenzoate | 1.5 mg |
| | Butyl Hydroxybenzoate | 0.75 mg |
| | Saccharin Sodium | 5.0 mg |
| | Sorbitol Solution | 1.0 ml |
| | Suitable Buffers | qs |
| | Suitable flavours | qs |
| | Purified Water to | 10 ml |

The hydroxypropyl methylcellulose is dispersed in a portion of hot purified water together with the hydroxybenzoates and the solution is allowed to cool to ambient temperature. The saccharin sodium flavours and sorbitol solution are added to the bulk solution. The compound of the invention is dissolved in a portion of the remaining water and added to the bulk solution. Suitable buffers may be added to control the pH in the region of maximum stability. The solution is made up to volume, filtered and filled into suitable containers.

EXAMPLE 12

Injection Formulation

| | % w/v |
|---|---|
| Compound of the invention | 1.00 |
| Water for injections B.P. to | 100.00 |

Sodium chloride may be added to adjust the tonicity of the solution and the pH may be adjusted to that of maximum stability and/or to facilitate solution of the compound of the invention using dilute acid or alkali or by the addition of suitable buffer salts. Antioxidants and metal chelating salts may also be included. The solution is clarified, made up to final volume with water and the pH remeasured and adjusted if necessary, to provide 10 mg/ml of the compound of formula (I).

The solution may be packaged for injection, for example by filling and sealing in ampoules, vials or syringes. The ampoules, vials or syringes may be aseptically filled (e.g. the solution may be sterilised by filtration and filled into sterile ampoules under aseptic conditions) and/or terminally sterilised (e.g. by heating in an autoclave using one of the acceptable cycles). The solution may be packed under an inert atmosphere of nitrogen.

Preferably the solution is filled into ampoules, sealed by fusion of the glass and terminally sterilised.

Further sterile formulations are prepared in a similar manner containing 0.5, 2.0 and 5% w/v of the compound of formula (I), so as to provide respectively 5, 20 and 50 mg/ml of the compound of formula (I).

We claim:

1. A compound of formula (I)

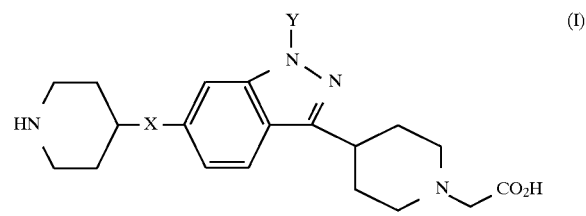

or a pharmaceutically acceptable derivative thereof, in which:

X represents either $CH_2$—$CH_2$ or CH=CH; and

Y represents a hydrogen atom or a phenylmethyl group, wherein the phenyl group is optionally substituted by one or more halogen atoms.

2. A compound as claimed in claim 1 in which X represents CH=CH.

3. A compound as claimed in claim 1 in which Y represents a hydrogen atom.

4. A compound as claimed in claim 1 in which X represents CH=CH in the (E) configuration.

5. {4-[6-(2-Piperidin-4-yl-(E)-vinyl)-1H-indazol-3-yl]-piperidin-1-yl}-acetic acid; or a pharmaceutically acceptable derivative thereof.

6. {4-[6-(2-Piperidin-4-yl-(E)-vinyl)-1H-indazol-3-yl]-piperidin-1-yl}-acetic acid hydrochloride, or a hydrate thereof.

7. A pharmaceutical composition comprising a compound of formula (I) or a pharmaceutically acceptable derivative thereof as defined in claim 1 in admixture with one or more physiologically acceptable carriers or excipients.

8. A method of treating a human or animal subject suffering from a thrombotic disorder, which method comprises administering to said subject an antithrombotical amount of a compound of formula (I) or a pharmaceutically acceptable derivative thereof as defined in claim 1.

9. A compound of formula (II):

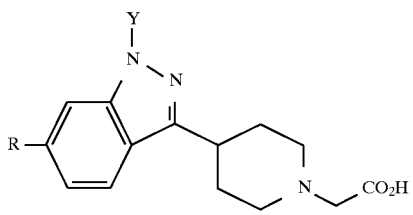

or a protected derivative thereof, wherein:
R represents a chlorine, bromine or iodine atom, or the group —OSO$_2$CF$_3$; and Y represents a hydrogen atom or a phenylmethyl group, wherein the phenyl group is optionally substituted by one or more halogen atoms.

10. A compound as claimed in claim 1 wherein the compound of formula (I) is in the form of a hydrochloride, hydrobromide, sulphate, phosphate, benzoate, naphthoate, hydroxynaphthoate, p-toluenesulphonate, methanesulphonate, sulphamate, ascorbate, tartrate, salicylate, succinate, lactate, glutarate, glutaconate, acetate, tricarballylate, citrate, fumarate, maleate, or sodium salt; or a solvate.

11. A process for the preparation of a compound of formula (I) or a pharmaceutically acceptable derivative thereof as defined in claim 1, which comprises:

(A) for the preparation of compounds of formula (I) in which X represents CH=CH reacting a compound of formula (II)

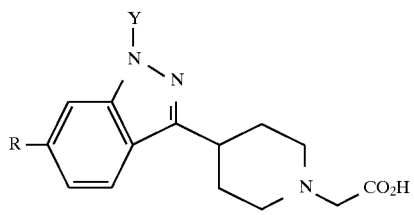

wherein R is a chlorine atom, a bromine atom, an iodine atom or a group —OSO$_2$CF$_3$, or a protected derivative thereof with a compound of formula (III)

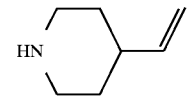

or a protected derivative thereof, or (B) interconverting a compound of formula (I) into another compound of formula (I), or (C) deprotecting a protected derivative of a compound of formula (I); and optionally converting a compound of formula (I) prepared by any one of processes (A) to (C) into a pharmaceutically acceptable derivative thereof.

* * * * *